United States Patent
Williams (10) Patent No.: US 7,180,594 B2
(45) Date of Patent: Feb. 20, 2007

(54) METHOD AND APPARATUS FOR VERIFYING PROPER OPERATION OF A PHOTOMETRIC DEVICE, SUCH AS A CELL DENSITY PROBE

(75) Inventor: Paul C. Williams, Livermore, CA (US)

(73) Assignee: Finesse Instruments, LLC.

( * ) Notice: Subject to any disclaimer, the term of this patent is extended or adjusted under 35 U.S.C. 154(b) by 425 days.

(21) Appl. No.: 10/856,885

(22) Filed: May 27, 2004

(65) Prior Publication Data
US 2005/0264816 A1  Dec. 1, 2005

(51) Int. Cl.
G01N 21/00 (2006.01)
G01J 3/42 (2006.01)

(52) U.S. Cl. .................... 356/436; 356/319
(58) Field of Classification Search ........... 356/436
See application file for complete search history.

(56) References Cited

U.S. PATENT DOCUMENTS

| | | | | |
|---|---|---|---|---|
| 3,609,047 A | * | 9/1971 | Marlow | 356/434 |
| 4,200,896 A | * | 4/1980 | Baumann | 345/55 |
| 4,692,883 A | * | 9/1987 | Nelson et al. | 356/319 |
| 4,744,657 A | * | 5/1988 | Aralis et al. | 356/319 |
| 4,866,644 A | * | 9/1989 | Shenk et al. | 356/319 |
| 5,125,747 A | * | 6/1992 | Sayegh et al. | 356/407 |
| 5,230,863 A | * | 7/1993 | Salpeter | 422/67 |
| 5,243,546 A | * | 9/1993 | Maggard | 702/90 |
| 5,248,937 A | * | 9/1993 | Holzle | 324/158.1 |
| 5,316,950 A | * | 5/1994 | Apitz et al. | 436/28 |
| 5,347,138 A | * | 9/1994 | Aqui et al. | 250/573 |
| 5,847,835 A | * | 12/1998 | Fukunaga | 356/436 |
| 6,125,789 A | * | 10/2000 | Gupta et al. | 118/723 E |
| 6,611,777 B2 | * | 8/2003 | Samsoondar | 702/104 |
| 6,696,362 B2 | * | 2/2004 | Rossman et al. | 438/680 |
| 6,711,516 B2 | * | 3/2004 | Samsoondar | 702/86 |
| 7,002,670 B2 | * | 2/2006 | Wariar et al. | 356/39 |
| 2001/0020123 A1 | * | 9/2001 | Diab et al. | 600/323 |

OTHER PUBLICATIONS

Aber-Instruments, "Theory of Dielectrics—The Basics of Dielectric Theory," retrieved Apr. 1, 2004 from http://www.aber-instruments.co.uk/page5a.htm.

(Continued)

*Primary Examiner*—Layla G. Lauchman
(74) *Attorney, Agent, or Firm*—Herbert Burkard (57) ABSTRACT

An in-situ technique is provided for automatically verifying proper operation of a photometric device, such as a cell density probe (CDP). The CDP has a first detector and a second detector. The first detector senses light that is transmitted from a light source of the CDP. The second detector senses light that has passed through an optical gap at a tip of the CDP, wherein the sensed light has been reduced in intensity due to light absorption. Electrical current provided to the light source is reduced, and the resultant values of a light characteristic (such as intensity) are sensed. These values from the detectors are compared against one or more predicted values. If the CDP is operating properly, the values from the detectors will be consistent with the predicted values. If there is a malfunction in the CDP, then the values from the detectors will be inconsistent with the predicted values.

26 Claims, 4 Drawing Sheets

OTHER PUBLICATIONS

Optek®, Bioprocess Fermentation Probe with NIST-traceable Validation Adapter.

Aquasant® AG, "Turbidimeters," retrieved Apr. 2, 2004 from http://www.aquasant.com/.

B. Braun Biotech International, "Fundalux® II—Turbidity Measurement System."

Optek® inline control, "Fermenter Control—Cell Growth/Biomass," www.optek.com.

Wedgewood Technology, "Model BT65—Cell Growth Sensor," www.wedgewoodtech.com.

Wedgewood Technology, "Model 950—Absorbance Monitor," www.wedgewoodtech.com.

"Cell Density Probes," retrieved Apr. 1, 2004 from http://www.mcindumation.com/Monitek/MonitekCelldensprobes.htm.

Mettler Toledo, "Growth Control of Biomass Using Turbidity Measurement," *Pharmaceutical News 2*.

OPTEK Technology Inc., "Understanding VCSEL's & LED's in Commercial Applications," Issue A, Jan. 2003, www.optekinc.com.

OPTEK Technology Inc., "Laser Safety Bulletin OPV Series, VCSEL," *Application Bulletin 221*, Issue 1.0, May 2003, www.optekinc.com.

OPTEK Technology Inc., "Vertical Cavity Surface Emitting Laser in TO-46 Package," Issue 3.2 Sep. 2003, www.optekinc.com.

Wedgewood Technology, "Model AF11—Solids Sensor," www.wedgewoodtech.com.

Mettler Toledo GmbH, "Full Range Turbidity Measurements—Brilliant Results for Effective Process Control," Jul. 2002, www.mtpro.com.

\* cited by examiner

METHOD AND APPARATUS FOR VERIFYING PROPER OPERATION OF A PHOTOMETRIC DEVICE, SUCH AS A CELL DENSITY PROBE

TECHNICAL FIELD

The present disclosure is generally related to photometric devices, and particularly but not exclusively relates to techniques to verify whether an optical absorbance measurement device, such as a cell density probe, is operating properly.

BACKGROUND INFORMATION

There are several types of photometric devices used in a variety of different applications. In general, photometric devices include devices that are used to measure or otherwise determine one or more characteristics of light, such as intensity, color, wavelength, or other characteristic.

One type of photometric device is an optical absorbance probe, which is used in the biotechnology, chemical, brewery, pulp and paper, fermentation, pharmaceutical, winery, and other sectors of industry and/or research. With biotech applications, one type of optical absorbance probe known as "cell density probes" are ordinarily used to monitor cell growth in a cell culture. In a typical implementation, live cells and some type of suitable growth agent (as well as possibly other additives) are placed in a vat or other vessel, with the growth agent, cells, and possibly other additives together forming a "broth" made up of liquid and suspended particulates (e.g., the cells). Conditions in the vat are then appropriately controlled to induce the cells to multiply and grow. The cells, once a sufficient amount have been grown, are harvested for various uses.

Cell density probes are used to monitor the cell growth in the vat at various times during the growing cycle, so as to ensure that the cells are growing at a proper rate and/or to verify whether a sufficient number of cells have been grown. Use of a cell density probe is an alternative to manual cell counting techniques, wherein cells in a sample from the vat are extracted and physically counted (and thus result in a high degree of error and is very labor intensive). In comparison, a density probe allows the number of cells to be automatically determined by correlation of light absorbance to cell density (e.g., the determined cell density can be correlated to the number of cells and/or cell growth rate in the broth).

A typical cell density probe includes a tip that has an optical gap. The cell density probe is immersed into the vat, such that the optical gap and tip are completely covered in the broth. A light is transmitted from a first end of the optical gap to second end of the optical gap. As the light passes through the optical gap, the cells present within the optical gap absorb a certain amount of the light. Therefore, the light received at the second end of the optical gap will have a lower intensity than the light transmitted from the first end of the optical gap, due to the absorbance of the light by the cells, which is typically expressed in terms of absorbance units (A.U.). The intensity of the received light decreases as the density of cells increase. Persons skilled in the art can correlate various intensities of the received light with growth rates and cell densities for the particular cell type that is involved. Accordingly, by monitoring the intensity of the received light over a period of time, the user of the cell density probe can determine if the growth rate is proceeding normally, if a sufficient number of cells have been grown, and/or whether a problem has occurred in the growing cycle.

For example, if the cell density probe provides a light intensity measurement that is higher than expected for that particular time in the growth cycle, then the high intensity measurement may be indicative of contamination or other environmental condition that is impeding the capability of the cells to grow properly.

In the biotech industry, particular importance is placed on clinical trials. Accordingly, it is in the best interest of companies seeking Federal Drug Administration (FDA) approval, for instance, to be able to readily provide documentation and other evidence that their equipment was calibrated and functioning properly, accurate measurements were taken, and other information to validate results. Of course, proper calibration of equipment (such as cell density probes) outside of the clinical trial environment is also desirable from a day-to-day operation point of view, whether for the biotech industry or for other industry or research involving the monitoring of cell growth cycles.

However, existing techniques to calibrate or otherwise verify the proper operational state of a cell density probe are impractical, insufficient, and prone to error. For instance, one technique for calibration is to first take the cell density probe offline, which involves removal of the cell density probe from the vat for calibration or calibration of the cell density probe prior to immersion in the vat. A neutral density filter, whose absorption (in A.U.) is known precisely, is then slid into or otherwise placed within the optical gap of the cell density probe's tip. The cell density probe is then activated such that light is transmitted from the first end of the optical gap and through the neutral density filter therein. Since the intensity of the transmitted light and the absorption of neutral density filter are both known quantities, the intensity of the light received at the second end of the optical gap should be consistent with the known quantities. For example, a neutral density filter having 1 A.U. corresponds to 90.00% absorbance. Thus, if there is a 10.00% detected intensity in the received light, as compared to the transmitted light, then the cell density probe is operating properly. For added verification, several neutral density filters, each having different grades of absorbance, can be sequentially placed in the optical gap to verify other detected intensity values. A higher-than-expected or a lower-than-expected detected intensity can be indicative of a malfunction in the cell density probe's electronics.

There are several disadvantages of using the above-described calibration technique. One disadvantage is that the cell density probe needs to be physically removed from the vat in order to perform the testing and calibration. This removal thus involves and requires physical user intervention, and further disturbs the operation of the device. Moreover, the testing and calibration is being performed offline out of the vat while the cell density probe's tip is not immersed in the broth, and therefore may not necessarily produce results that are representative of actual conditions in the vat.

BRIEF SUMMARY OF THE INVENTION

In one aspect, a method to test a photometric device usable for a light absorbance application is provided. The method includes changing a signal supplied to a light source of the photometric device, with the supplied signal being usable to activate the light source to emit light. A first signal representative of the light emitted from the light source is obtained. A second signal is obtained that is representative of the light emitted from the light source after at least some of the emitted light has passed through an optical gap of the photometric device. The method determines whether the photometric device is operating properly based on a comparison between: a) an obtained value, associated with either one or both of the first and second signals, and b) at least one reference value, wherein the determination can be performed independently of whether any of the emitted light is absorbed as it passes through the optical gap.

BRIEF DESCRIPTION OF THE SEVERAL VIEWS OF THE DRAWINGS

Non-limiting and non-exhaustive embodiments are described with reference to the following figures, wherein like references numerals refer to like parts throughout the various views unless otherwise indicated.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the claimed invention.

As an overview, one embodiment provides an in-situ technique for verifying proper operation of a photometric device, such as a cell density probe (CDP). The CDP is provided with a first detector and a second detector. The first detector senses light that is transmitted from a light source of the CDP. The second detector senses light that has passed through an optical gap at a tip of the CDP, wherein the sensed light has been reduced in intensity, as compared to the transmitted light, due at least in part to absorption caused by cells present in the optical gap.

According to an embodiment, electrical current provided to the light source is reduced, and the resultant values of a light characteristic (such as intensity) at the first and second detectors are sensed. These sensed values are compared against predicted values. If the CDP is operating properly, the sensed values will be consistent with the predicted values. If there is a malfunction in the CDP (such as electrical or mechanical malfunctions that can affect the transmission and detection of the light, as well as the processing thereof), then the sensed values will be inconsistent with the predicted values.

The current reduction and subsequent detection and comparison can be performed automatically without having to manually insert neutral density filters into the optical path. Software can be provided to perform the various testing/verification operations, and can further be provided to repeatedly perform such operations at scheduled intervals based on user preferences and/or at any user-desired time. The various results of the verification operations can be logged by a control system of the CDP. Therefore, an embodiment allows verification of operation of the CDP while in-situ without disturbing operation of the CDP, without interrupting the growth cycle or other associated processes, and/or without requiring physical user interaction with the CDP. In an embodiment and as will be more clearly described later below, verification of proper operation of the CDP regardless of what is present in the optical gap when the verification/testing is performed.

For purposes of illustration and explanation, one embodiment will be described herein in the context of a CDP that is used for turbidity measurements, such as determination of cell density in biotech applications. It is appreciated that other embodiments may be implemented for other types of photometric devices that are used for other types of measurements and/or for other types of industrial/academic applications.

Figure 1:
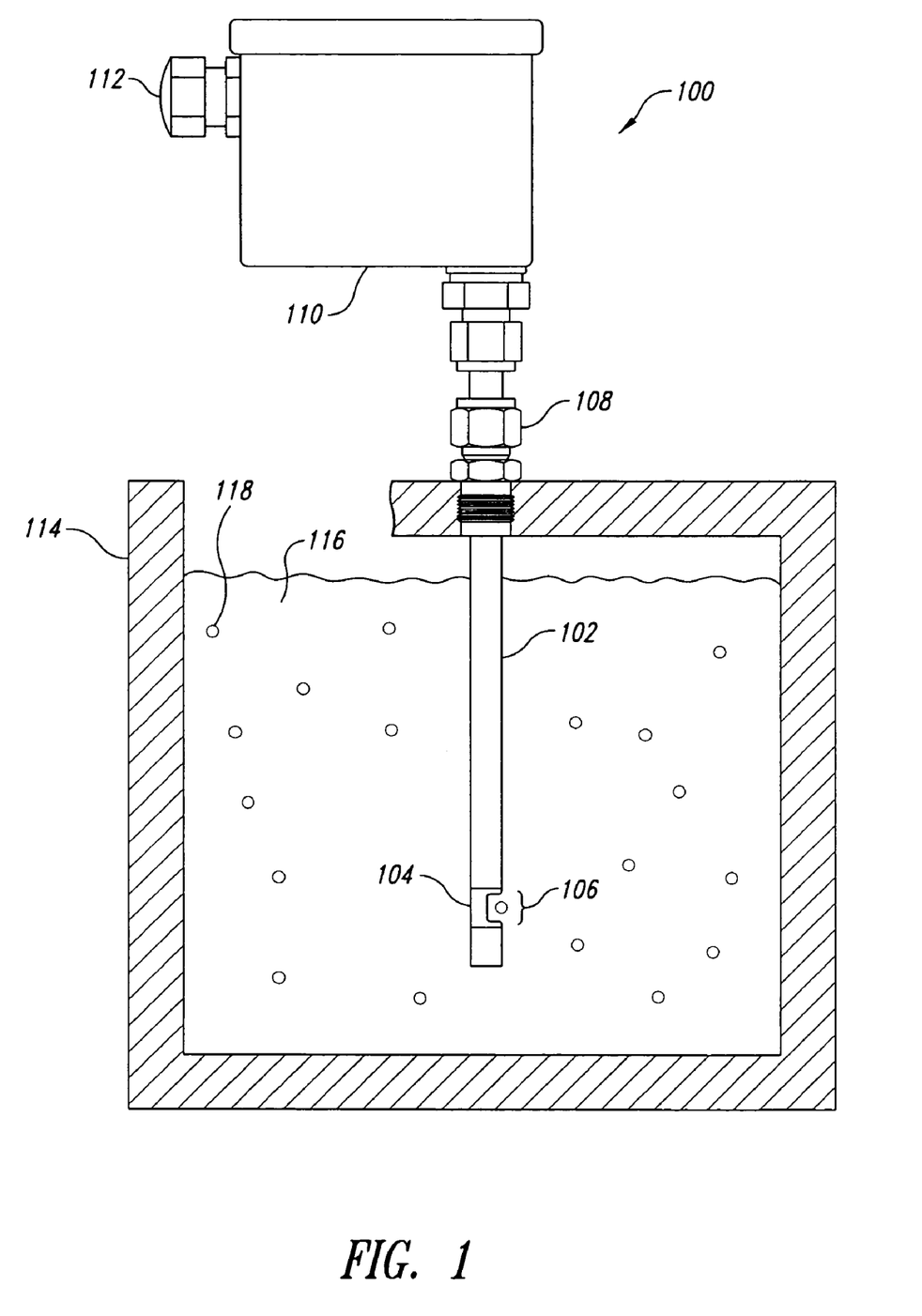
FIG. 1 is a side view of an embodiment of a cell density probe while in operation.

FIG. 1 shows an example photometric device, such as a CDP 100, according to an embodiment. The CDP 100 includes a generally tubular probe section 102 having a tip section 104. An example diameter of the probe section is 12 mm, which is a smaller diameter than other types of CDPs, thereby providing the CDP 100 with a more compact and lightweight structure for ease of placement into and removal from receptacles of vats.

The tip section 104 includes or otherwise defines an optical gap 106. One or more fittings 108 that couple the probe section 102 to a housing 110, which houses software, hardware, electronics, communication components, or other elements associated with operation of the CDP 100. According to an embodiment, the CDP 100 includes an interface 112 that can be used to provide wireless and/or wired communications with the CDP 100, such as programming the CDP 100, reading data therefrom, obtaining verification results, and so forth.

The CDP 100 of FIG. 1 is shown in its operating environment. In this example, the CDP 100 is mounted to or otherwise coupled to a vat 114. The vat 114 holds a liquid medium 116. Cells 118 (or other organisms, bacteria, organic matter, etc.) are grown in the medium 116. The probe section 102 of the CDP 100 is positioned such that the tip section 104 is immersed in the medium 116. This immersion allows a representative amount of the cells 118 to occupy the optical gap 106. Therefore, when a light is transmitted through the optical gap 106, the cells 118 present therein will absorb some of the transmitted light. As will be described in further detail below, the detected absorbance of light can be correlated with an amount of electrical current reduction to power a light source of the CDP 100 and then compared to predicted values, so as to determine whether the CDP 100 is functioning properly.

Figure 2:
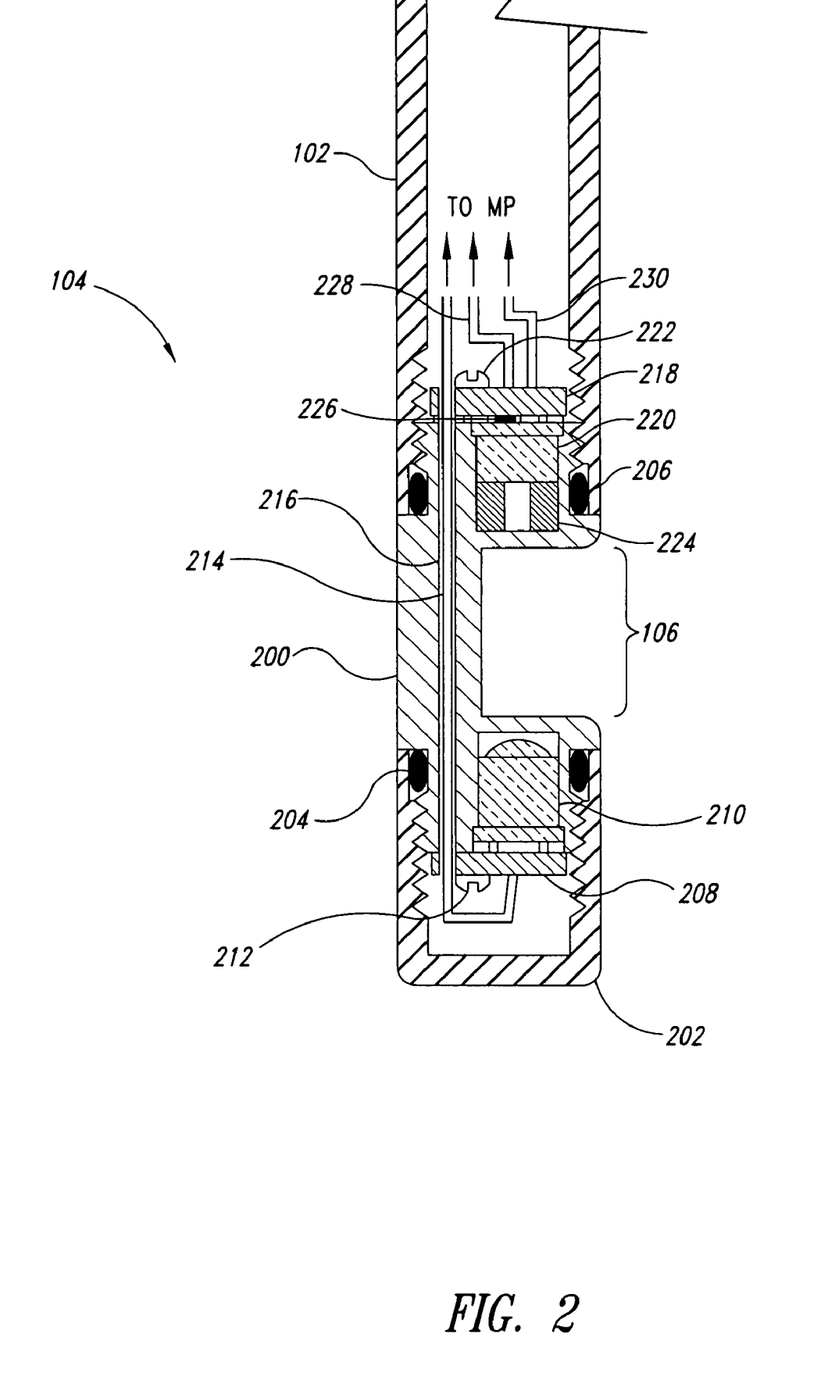
FIG. 2 is a side cross-sectional view of a tip section of the cell density probe of FIG. 1 in more detail.

FIG. 2 is a cross-sectional side view of the tip section 104 shown in more detail. It is appreciated that the depicted structure of the tip section 104 is merely for explanatory purposes. Other embodiments may be implemented for tip sections 104 that have different structures or components. A general description of one embodiment of the tip section 104 will be provided herein, and further detailed descriptions can be found in U.S. Provisional Patent Application Ser. No. 60/575,119 entitled "VCSEL FOR OPTICAL ABSORBANCE MEASUREMENTS, SUCH AS A VCSEL FOR A CELL DENSITY PROBE (CDP)," filed May 27, 2004, assigned to the same assignee as the present application, and which is incorporated by reference herein in its entirety.

The probe section 102 has hollow tubular shape, made out of metal for instance, and has a threaded end that is coupleable to the tip section 108. The tip section 104 of one embodiment comprises a sensor head 200 made from an optically semi-transparent material. In one example embodiment, the sensor head 200 is made of a molded polytetrafluoroethylene material, such as Teflon®. In other embodiments, the sensor head 200 can be made from sapphire, glass, plastic, or other optically transparent or semi-transparent material. The sensor head 200 may include threaded portions that mate with the threaded end of the probe section 102 and with threads of a sensor cap 202 (which itself may be made from the same material as the probe section 102). The threaded couplings, plus O-rings 204 and 206 (made from an ethylene-propylene-diene-monomer material, for example) ensure that the medium 116 or other foreign material do not enter the interior of the tip section 104.

The length of the optical gap 106 can vary depending on the particular application involved. For example, shorter optical gaps can be provided in situations where the particular cells 118 have higher absorbencies as compared to other types of cells, or different optical gap lengths can be provided for biotech applications versus brewery applications, for instance. Detailed discussion for determining the proper optical gap length will not be provided herein, since such details would be familiar to those skilled in the art having the benefit of this disclosure.

Adjacent to the sensor cap 202 on one end of the optical gap 106, the sensor head 200 is shaped to accommodate a photodetector assembly, and to insulate the photodetector assembly from the medium 116. The photodetector assembly of one embodiment comprises a circuit board 208 having a photodetector 210 (such as a photodiode) mounted thereon. A screw 212 or other suitable attachment mechanism (such as glue) can be used to fixedly attach the circuit board to the sensor head 200.

The sensor head 200 is defined with a channel 214 that accommodates one or more electrical leads 216 coupled to the photodetector 210. These electrical leads 216 can carry electrical signals representative of the intensity of light detected by the photodetector 210, after that light has traversed through the optical gap 106. The electrical leads 216 are coupled to conditioning electronics. The electrical signals are converted to digital values that are read by a controller, microprocessor, digital signal processor, or other processor that can cooperate with software to determine or otherwise calculate cell density (or an approximation thereof) based on the values of the detected light intensity, and/or to verify proper operation of the CDP 100.

At the other end of the optical gap 106, the sensor head 200 is shaped to accommodate a light source assembly, as well as being shaped to insulate the light source assembly from the medium 116. The light source assembly of one embodiment comprises a circuit board 218 having a light source 220 mounted thereon. In one embodiment, the light source 220 comprises a Vertical-Cavity Surface-Emitting Laser (VCSEL). In other embodiments, the light source 220 can comprise a light emitting diode (LED), other type of laser, incandescent light bulb, infrared light bulb, lamp, or other type of light source. A screw 222 or other suitable attachment mechanism (such as glue) can be used to fixedly attach the circuit board to the sensor head 200. Spacers 224 (made from an acetal resin material, such as black Delrin®, for example) can be provided to prevent light from the light source 206 from scattering and propagating to the photodetector 210 via the solid material of the sensor head 200, rather than through the optical gap 106.

According to one embodiment, a reference photodetector 226 is also mounted on the circuit board 218. The photodetector 226 operates to detect the intensity of the light emitted from the light source 220, prior to reduction of the light's intensity due to absorbance by cells 118 in the optical gap 106. The photodetector 226 can measure light directly output from the light source 220 and/or can measure light scattered or reflected therefrom.

One or more electrical leads 228 couples the photodetector 226 to conditioning electronics, which are in turn coupled to the processor, thereby allowing detected intensity values from the photodetector 226 to be provided to the processor. One or more electrical leads 230 is coupled between the light source 220 and the electronics, which are in turn coupled to the processor, thereby allowing the light source 220 to be turned ON or OFF, and to change (such as reduce or increase) the current signal supplied to the light source 220 during verification operations.

Figure 3:
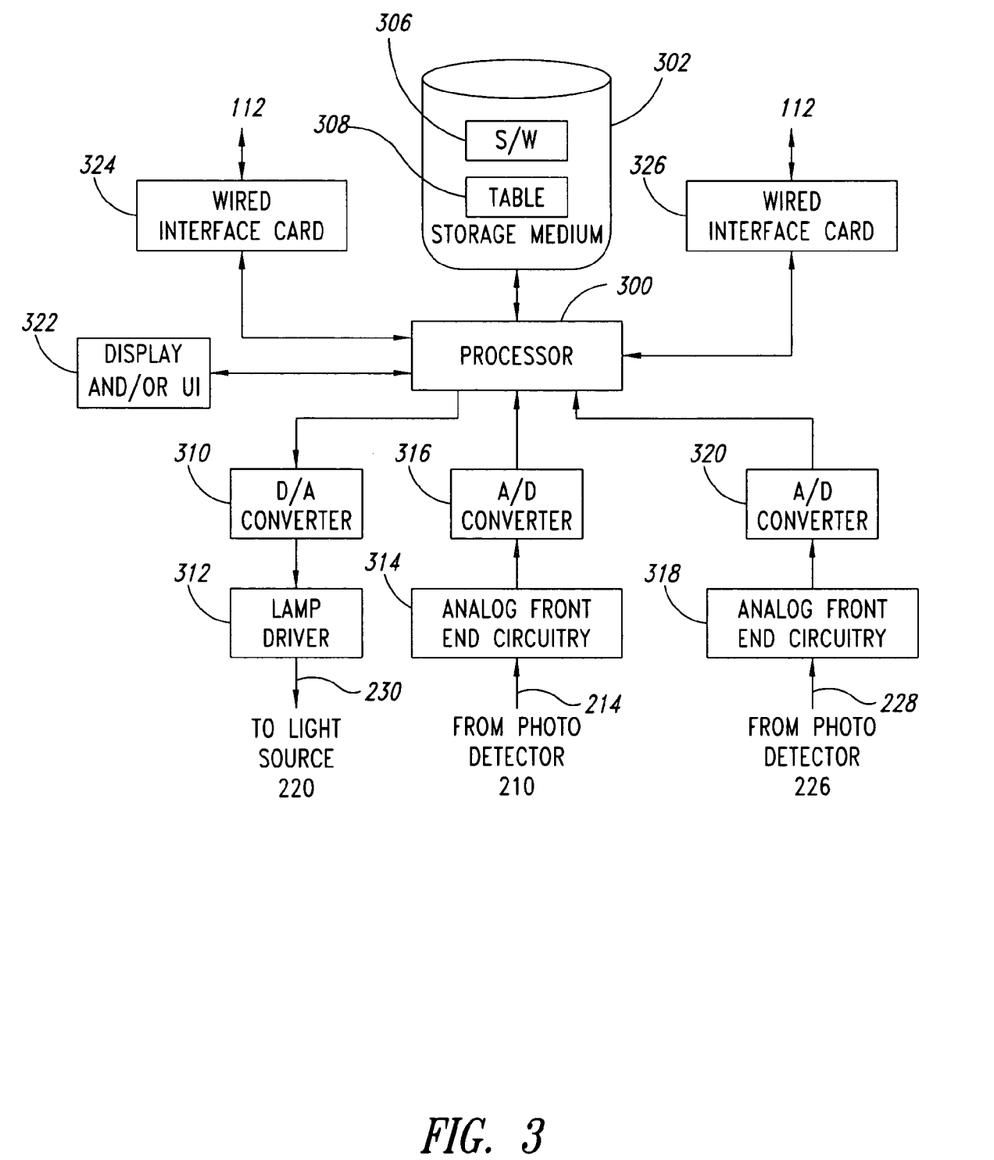
FIG. 3 is a block diagram of electronic and software components of the cell density probe of FIG. 1 according to an embodiment.

FIG. 3 depicts at least some of the electronic and software components of the cell density probe 100 according to an embodiment. FIG. 3 is only intended to illustrate components that are useful for understanding operation of an embodiment. Therefore, it is appreciated that the cell density probe 100 can include other electronic and software components, which are not shown in FIG. 3 for the sake of brevity and simplicity of explanation.

The various components shown in FIG. 3 can be contained in the housing 110. The CDP 100 includes conditioning electronics and at least one processor 300, which may be embodied as a microprocessor, controller, microcontroller, digital signal processor, or other type of processor or combination thereof. The processor 300 is coupled to a machine-readable storage medium 302, which may be embodied as RAM, ROM, hard disk, CD, diskette, cache, buffer, or other type of memory. The storage medium 304 can store software 306 or other machine-readable instruction executable by the processor 300. In an embodiment, the software 306 can cooperate with the processor 300 to determine light absorption and cell density based on intensity of light detected by the photodetector 210. Also in an embodiment, the software 302 can cooperate with the processor 300 to verify whether the CDP 100 is operating properly based on a comparison of detected drops in light intensity with expected drops in light intensity.

The expected or predicted drops in light intensity may comprise at least some of the data stored in a lookup table 308 in the storage medium 302. Other possible values in the lookup table 308 can include, but not be limited to, electrical current values, light intensity values associated with the photodetector 210, light intensity values associated with the photodetector 226, A.U. values corresponding to various cell densities, identifiers associated with types of media 116 or types of cells 118, lengths of the optical path 106, and other values.

While a lookup table 308 is shown and described herein with respect to operations associated with verifying proper operation of the CDP 100, it is appreciated that other techniques for performing such operations may be used. For example, calculations may be performed by the processor 300 alternatively or in addition to consulting the lookup table 308. Certain values may be stored as dynamic or fixed variables, alternatively or in addition to using the lookup table 308.

To control the operation of the light source 220, one embodiment of the CDP 100 includes at least one digital-to-analog (D/A) converter 310 coupled to the processor 300. The D/A converter 310 converts digital control signals from the processor 300 into analog control signals, which are in turn provided to a lamp driver 312 coupled to the light source 220 by way of the electrical lead(s) 230. The analog control signals, according to one embodiment, can control the amount of current that the lamp driver 310 supplies to the light source 220. Thus, the processor 300 can selectively increase or decrease the supplied current, and correspondingly change the intensity of the light emitted by the light source 220 across the optical gap 306.

With regards to processing light intensities detected by the photodetector 210, the CDP 100 includes analog front end circuitry 314 coupled to the photodetector 210 by way of the electrical lead(s) 214. The circuitry 314 is in turn coupled to an analog-to-digital (A/D) converter 316, which convert the analog signals representative of the detected light intensities into digital signals for the processor 300.

The CDP 100 makes an absorbance measurement, for which the fundamental unit for this measurement is Absorbance Units or A.U. Absorbance is defined as the logarithm (base 10) of the ratio of the intensity of the light transmitted through a reference medium ($I_0$) to the intensity of the light transmitted through the medium of interest ($I_T$):

$$\text{Absorbance(A.U.)} = \log \frac{I_0}{I_T} = -\log \frac{I_T}{I_0} = -\log\left(\frac{\% \text{ transmitted light}}{100}\right),$$

wherein the reference is defined as 100% transmitted light.

If a silicon photodiode is used as the photodetector 210, the photodetector 210 outputs a current that is proportional to the intensity of the light incident on it over a very wide range of approximately 1 mA to 1 nA, for example. Therefore, assuming that the light through the reference medium generated a photodiode current of 1 mA, this value would be considered the "zero" point or reference current. If the light through the medium of interest generated this same current of 1 mA, the absorbance would be 0 A.U. For a measured photodiode current of 100 uA, absorbance would be 1 A.U. Measured currents of 10 uA, 1 uA, 100 nA, 10 nA, and 1 nA would correspond to 2, 3, 4, 5 and 6 A.U. readings respectively.

Since a several decade range in current is produced by the photodetector 210, direct linear A/D conversion would need a high number of bits or a variable gain amplifier in from the of the A/D converter 316 with wide gain range. Therefore, one embodiment of the circuitry 314 includes an analog logarithmic amplifier, which receives a current input and provides a log ratio of the current input relative to a reference current.

With regards to the photodetector 226, the CDP 100 includes analog front end circuitry 318 coupled to the photodetector 226 by way of the electrical lead(s) 228. The circuitry 318 is in turn coupled to an A/D converter 320, which converts analog signals representative of the light intensity detected by the photodetector 226 into digital signals for the processor 300. The circuitry 318 can also include an analog logarithmic amplifier.

While separate analog front end circuitry 214/218 and A/D converters 316/320 are shown, it is appreciated that at least some of these components may be shared or common circuitry in another embodiment. For instance, a single A/D converter may be used to convert analog signals from both of the photodetectors 210 and 226.

One embodiment of the CDP 100 includes a display 322 or other suitable user interface (UI). The display 322 can be used to present data, such as calculated cell densities, time, detected electrical current values, detected intensity levels for the photodetectors 210 and 226, intensity drop per current reduction, and other data. The user can use the display 322 in conjunction with the UI to set various parameters related to operation of the CDP 100, including setting parameters for performing the verification processes (e.g., time intervals between verification checks, amount of current to reduce, conditions for providing an alert if the verification process provides unexpected results, values for comparison, and so forth).

Alternatively or in addition to directly reading and entering data via the display 322 and user interface, one embodiment of the CDP 100 allows communication via wired or wireless mechanisms. For example, CDP 100 can include a wired interface card 324 (which is in turn coupled to the interface 112) that can allow serial or parallel data to be exchanged between an external device (such as a personal computer) and the processor 300. With this wired connection, the user can analyze data (such as verification-related data) provided by the CDP 100 on the personal computer, or program the CDP 100 from the personal computer. A non-limiting example of the wired interface card 324 is a Foundation Fieldbus interface board.

Alternatively or in addition to the wired interface card 324, the CDP 100 can include a wireless interface card 326, which allows the user to communicate with the CDP 100 using a wireless device (such as a PDA, mobile laptop, cellular telephone, Blackberry, and so forth) via a wireless connection. An example of the wireless interface card 326 is a Bluetooth and web server board. It is appreciated that either or both of the cards 324 and 326 can be used in conjunction with Internet connectivity to allow the user to control and monitor the verification process or other operation related to the CDP 100.

Figure 4:
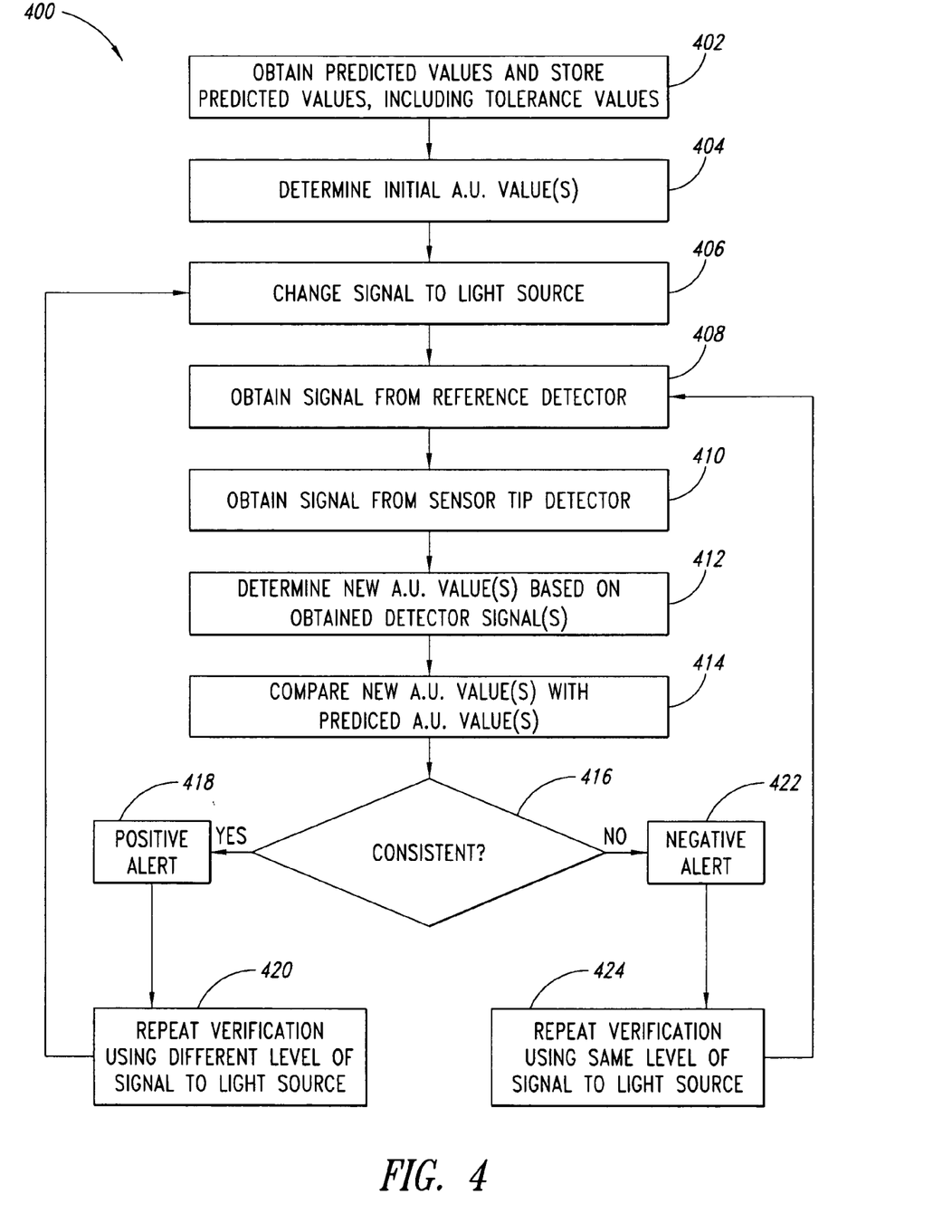
FIG. 4 is a flowchart depicting a verification process for the cell density probe of FIG. 1 according to an embodiment.

FIG. 4 is a flowchart 400 depicting a verification process for the cell density probe 100 according to an embodiment. Such a verification process can be used, for instance to determine whether the cell density probe is functioning properly. At least some of the elements of the flowchart 400 can be embodied in software or other machine-readable instruction stored on a machine-readable medium, such as the software 306 stored on the storage medium 302. It is appreciated that the various operations depicted in the flowchart 400 need not necessarily occur in the exact order shown and that certain operations can be added, removed, modified, combined, or any combination thereof.

Initially at a block 402, certain predicted values are obtained and stored. For example, the lookup table 308 is populated with reference values that may be used for comparison with actual values that are obtained during the verification process. In one embodiment, the reference values that are stored in the lookup table may include at least one or more of the following:

tolerance values between determined changes in A.U. values at either one or both of the photodetectors 210 and 226, and expected/predicted changes in A.U. values at these photodetectors when the signal to the light source 220 is changed;

tolerance values between changes in A.U. values at the photodetectors 210 and 226, in which such changes in A.U. values should be at least substantially equal (but with some possible amount of difference) for a given change in the signal supplied to the light source 220, if the photometric device 100 is operating properly;

values of signal level supplied to the light source 220, along with tolerance values if desired;

expected changes in A.U. levels at either or both the photodetectors 210 and 226 corresponding to changes in signal level supplied to the light source 220;

changes in output level of the light source 220 in response to known changes in supplied signal, and from these output level changes, the expected changes in A.U. values at the photodetectors 210 and 226 in response to the known changes in supplied signal; and/or other reference values that will be apparent to one skilled in the art having the benefit of this disclosure.

In one embodiment, such reference values can be manually programmed into the lookup table 308. Alternatively or additionally, such reference values can be empirically and/or heuristically determined from several CDPs 100, and then averaged or otherwise generalized for the lookup table 308. Of course, it is to be appreciated that other techniques may be used at the block 402 to obtain reference or other baseline values for the lookup table 308, or for other mechanism alternatively or additionally to the lookup table 308. For example, alternatively or in addition to conversion to A.U. readings, resultant current signal levels (such as amplitudes of the signals) may be recorded from each photodetector 210 and 226 as the current signal to the light source is dropped or otherwise changed. Such a technique provides an indication of detected signal changes that correspond to different levels of current changes to the light source 220.

After the baseline and/or reference values are programmed into the CDP 100, the CDP 100 may be placed online by mounting or otherwise deploying the CDP 100 into the vat 114 containing the medium 116 and cells 118, thereby allowing in-situ verification of the proper operation of the CDP 100. The cells 118 are then allowed to grow at their particular growth cycle. At any suitable time during the growth cycle (e.g., user-initiated or automatically determined instances of time wherein an A.U. reading is to be performed), a signal (such as a current signal) is supplied to the light source 220 at some operating level such that the light source 220 is activated and emits light. Some of this emitted light is absorbed by the cells 118 in the optical gap 106, and therefore, the CDP 100 can obtain an initial A.U. reading at a block 404 from the photodetectors 210 and 226. For example, the initial A.U. values may be 0.50 A.U. on the photodetector 210 and 0.02 A.U. on the photodetector 226.

Next at a block 406, the signal to the light source 220 is changed, for example, reduced from a full rated level to a lower level. It is also possible to perform the verification by increasing the signal to the light source 220. For purposes of simplicity of explanation herein, the changing of the signal level to the light source 220 will be described in the non-limiting context of reducing current level supplied to the light source 220. For example, in the context of a VCSEL or other types of devices as the light source 220, the signal reduction involves reduction of supplied current level. With other types of devices, the signal reduction can involve reduction in voltage level.

If the signal level to the light source 220 is reduced at the block 406 by 90%, for example, then a change of substantially 1 A.U. is expected at both of the photodetectors 210 and 226 (e.g., the A.U. values at the photodetectors 210 and 226 are compared with each other) according to a first embodiment of the verification technique. In a second embodiment of the verification technique, the signal level to the light source 220 is changed at the block 406, and the determined actual A.U. changes at the photodetectors 210 and 226 are compared with respective expected changes in A.U. level stored in the lookup table 308. Both of these verification embodiments will be described next in further detail in connection with the subsequent blocks in the flowchart 400.

Next at blocks 408 and 410, respectively, the signals received from the reference photodetector 226 and from the photodetector 210 at the tip section 104 across the optical gap 106 are obtained. Such signals are representative of the intensity or amount of light incident thereon in an embodiment, and may be processed by the various circuitry and other elements depicted in FIG. 3 (such as A/D conversion). In one embodiment, such signals from the photodetectors 210 and 226 are current signals. At a block 412, new A.U. value(s) at either or both the photodetectors 210 and 226 can be determined based on the obtained current signals. In an embodiment, the determination of new A.U. values can include a determination of changes in A.U. values, as compared to the initial A.U. values obtained at the block 404, via accessing of the lookup table 308 and/or via calculation.

According to the first embodiment of the verification technique, the processor 300 can compare the determined changes in A.U. value obtained from the reference photodetector 226 with the determined change A.U. value at the photodetector 210 at a block 414 to confirm that these A.U. value changes are at least substantially equal to one another and consistent with the level of current change to the light source 220. That is, the change in A.U. level at these photodetectors 210 and 226 should be substantially the same, regardless of what was in the optical gap 106 when the test was begun. Such a comparison at the block 414 and at a block 416 can involve using the lookup table 308 to apply a tolerance value between the compared A.U. values from the photodetectors 210 and 226 for a given current level change, so as to determine whether the A.U. value changes are sufficiently equal.

In the second embodiment of the verification technique, the change in A.U. value at each of the photodetectors 210 and 226 are individually compared at the block 414 with respective expected A.U. value changes. Such a comparison can be performed by consulting the lookup table 308, such as by locating a field having a value corresponding to the present input current change, and then comparing the determined A.U. values of the detected signals at the photodetectors 210 and 226 with respective expected/predicted A.U. values indicated by the lookup table 308 for that particular input current value level.

At the block 416, the processor 300 determines whether there is a match between the obtained changes in A.U. value(s) and stored/reference A.U. value(s) in the lookup table 308. Such a determination of consistency and/or match between the expected and actual A.U. values can be performed at the block 416 for either one or both of the first and second embodiments of the verification techniques. In an embodiment, a substantially exact match is required between the actual and expected values. In other embodiments, the user can specify a desired degree of error or deviation (i.e., the tolerance values) between the obtained values and the stored values to determine whether there is a sufficient match or other consistency that would be indicative of a properly operating CDP 100.

If there is a match or other result that is consistent with prediction, then a positive alert may be provided at a block 418. For example, the display 322 may provide a visual indicator (such as a green light) and/or audio indicator (such as a short beep) to indicate that the CDP 100 is operating properly. For further verification, the process described above can be repeated at a block 420, wherein the current signal supplied to the light source 220 is further lowered to determine if the resulting values are consistent with values stored in the lookup table 308 for that particular current level.

Back at the block 416, however, if the processor 300 does not locate a matching A.U. entry at the block 416, then a negative alert may be generated by the display 322 at a block 422 (such as a red light or a long beep). With this negative alert, the user can decide to repeat the verification at a block 424 for the same current level supplied to the light source 220, so as to confirm or otherwise determine whether the CDP 100 is truly malfunctioning.

Therefore, embodiments of the verification technique can confirm that the measurement electronics, signal conditioning electronics, light source driver circuitry, software, and/or other elements of the CDP 100 are operating properly or as expected. With the described embodiments, relative changes in photodetector outputs in response to changes in signal supplied to the light source 220 are examined, without the requiring neutral density filters or placing the CDP 100 in a zero solution (i.e., 100% transmission without absorbance) for reference purposes. It is clear from the described verification embodiments that the testing can be performed independently of whether there is anything in the optical gap 106 that is absorbing light.

The above description of illustrated embodiments, including what is described in the Abstract, is not intended to be exhaustive or to limit the invention to the precise forms disclosed. While specific embodiments and examples are described herein for illustrative purposes, various equivalent modifications are possible within the scope of the invention and can be made without deviating from the spirit and scope of the invention.

For instance, the foregoing detailed description has set forth various embodiments of the devices and/or processes via the use of block diagrams, schematics, and examples. Insofar as such block diagrams, schematics and examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the software mechanisms of taught herein for verifying proper operation of a photometric device are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

A photodetector in the form of a photodiode has been described with regards to the photodetectors 210 and 226. The photodetectors 210 and 226 have also been described with respect to generating current signals that are representative of the light incident thereon. It is appreciated that other types of photodetectors (and their respective signals) may be implemented with other embodiments. For example, voltage signals, wireless signals, optical signals, or other signals may be used to represent one or more characteristics of light (such as intensity, wavelength, color, and the like) detected by a photodetector. The photodetectors 210 and 226 may be implemented as phototransistors, photoresistors, charge coupled devices (CCDs), or other photosensitive devices in other embodiments.

Techniques modified from or different from the technique shown in FIG. 4 may be used to verify the proper operation of the CDP 100. For instance, the technique of FIG. 4 involves a comparison of actual determined A.U. with a predicted A.U. for a particular reduced supply current. It is appreciated that the verification can be performed by comparing the drop in signal levels from either or both of the photodetectors 210 and 226 with expected drops, if the supply current is reduced to a certain level. As such, variables alternatively or additionally to just A.U. values may be used to determine whether the CDP 100 is operating properly.

As yet another example, a technique has been described herein with regards to reducing a current signal provided to the light source 220. Other embodiments can be provided wherein the current signal (or other signal) starts at some low level and then progressively increased to a full rated level, while performing verification at each signal level.

These and other modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. A method to test a photometric device usable for a light absorbance application, the method comprising the steps of:
   i) changing a signal supplied to a light source of the photometric device, the supplied signal usable to activate the light source to emit light;
   ii) obtaining a first signal representative of the light emitted from the light source;

iii) obtaining a second signal representative of the light emitted from the light source after at least some of the emitted light has passed through an optical gap of the photometric device; and iv) determining whether the photometric device is operating properly based on a comparison between: a) an obtained value, associated with either one or both of the first and second signals, and b) at least one reference value, wherein the determining can be performed independently of whether any of the emitted light is absorbed as it passes through the optical gap, and wherein steps i) through iv) are automatically performed in-situ while at least a portion of the photometric device is immersed in a medium having cells growing therein and wherein the results of steps i) through iv) are logged by a control system.

2. The method of claim 1 wherein changing the signal supplied to the light source includes changing the level of the current supplied to the light source.

3. The method of claim 2 wherein changing the level of the current supplied to the light source comprises reducing the level of the current supplied to the light source.

4. The method of claim 1 wherein determining whether the photometric device is operating properly based on the comparison between the obtained value, associated with either one or both of the first and second signals, and at least one reference value includes:
   comparing obtained absorbance unit value changes associated with the first and second signals with each other; and
   determining if the compared absorbance unit value changes are consistent with one another and with an expected absorbance unit value change.

5. The method of claim 1 wherein comparing the obtained value with at least one reference value includes comparing the obtained value with at least once reference value in a lookup table.

6. The method of claim 1 wherein determining whether the photometric device is operating properly based on the comparison between the obtained value, associated with either one or both of the first and second signals, and at least one reference value includes:
   comparing obtained absorbance unit value changes associated with either or both the first and second signals with each other; and
   determining that the photometric device is operating properly if the compared absorbance unit value changes are consistent with one another and consistent with an expected absorbance unit value change.

7. The method of claim 1, further comprising programming the photometric device with at least one reference value, including at least one tolerance value.

8. The method of claim 1, further comprising repeating the determining of whether the photometric device is operating properly for each of a plurality of other levels of the supplied signal.

9. An article of manufacture comprising a photometric device that is usable for a light absorbance application, the article of manufacture comprising:
   a machine-readable medium having instructions stored thereon and executable by the processor to cause a processor to test the photometric device by:
   i) changing a signal supplied to a light source of the photometric device, the supplied signal usable to activate the light source to emit light;
   ii) obtaining a first signal representative of the light emitted from the light source;

iii) obtaining a second signal representative of the light emitted from the light source after at least some of the emitted light has passed through an optical gap of the photometric device; and iv) determining whether the photometric device is operating properly based on a comparison between an obtained value, associated with either one or both of the first and second signals, and at least one reference value wherein the instructions executable by the processor are executed in-situ while the photometric device is deployed and substantially without interruption of operation of the photometric device and without regard to light absorbance in an optical gap of the photometric device.

10. The article of manufacture of claim 9 wherein the instructions to change the supplied signal includes instructions to change the level of the current supplied to the light source.

11. The article of manufacture of claim 9 wherein the instructions to determine whether the photometric device is operating properly based on the comparison between the obtained value, associated with either one or both of the first and second signals, and at least one reference value include instructions to:
   i) compare obtained absorbance unit value changes associated with the first and second signals with each other; and
   ii) determine that the photometric device is operating properly if the compared absorbance unit value changes are consistent with one another and consistent with an expected absorbance unit value change.

12. The article of manufacture of claim 9 wherein the instructions to determine whether the photometric device is operating properly based on the comparison between the obtained value, associated with either one or both of the first and second signals, and at least one reference value include instructions to:
   i) compare obtained absorbance unit value changes associated with either or both the first and second signals with respective predicted absorbance unit value changes; and
   ii) determine that the photometric device is operating properly if the respective compared absorbance unit value changes are consistent.

13. The article of manufacture of claim 9 wherein the instructions to compare the obtained value with the reference value includes instructions to compare the obtained value with at least one reference value in a lookup table, including instructions to apply a tolerance value to the comparison.

14. The article of manufacture of claim 9 wherein the instructions to obtain the first and second signals include instructions to process signals representative of intensity of the light.

15. A system, comprising:
   a photometric device including a light source for performing an optical absorbance determination comprising:
   i) means for changing a signal supplied to the light source, the supplied signal being usable to activate the light source to emit light;
   ii) means for obtaining a first signal representative of the light emitted from the light source;
   iii) means for obtaining a second signal representative of the light emitted from the light source
   iv) means after at least some of the emitted light has passed through an optical gap of the photometric device for determining whether the photometric device is operating properly based on a comparison between an obtained value, associated with either one or both of the first and second signals, and at least one reference value;

v) means for communicating to and from the photometric device;

vi) display means for presenting information related to operation of the photometric device;

vii) user interface means for allowing user interaction with the photometric device; and viii) means for allowing the photometric device to be tested in-situ for a cell density application.

16. The system of claim 15 wherein the means for determining whether the photometric device means is operating properly based on the comparison between the obtained value, associated with either one or both of the first and second signals, and at least one reference value includes means for comparing obtained absorbance unit value changes with one another and with at least one reference absorbance unit value change.

17. The system of claim 15 wherein the means for determining whether the photometric device means is operating properly based on the comparison between the obtained value, associated with either one or both of the first and second signals, and at least one reference value includes means for comparing a detected change associated with either or both the first and second signals with a respective predicted change.

18. A photometric apparatus usable for a light absorbance application, the apparatus comprising:

a light source that can supplied with a signal that can cause the light source to emit light;

a first detector to detect a characteristic of the light emitted from the light source;

a second detector to detect a characteristic of the light emitted from the light source after at least some of the light has passed through an optical gap;

a processor to control application of the signal supplied to the light source, wherein the processor can determine whether a malfunction may exist if there is a predetermined difference between an obtained value, associated with either one or both of the first and second signals, and at least one reference value;

means for communicating to and from the photometric apparatus;

display means for presenting information related to operation of the photometric apparatus;

user interface means for allowing user interaction with the photometric apparatus; and means for allowing the photometric apparatus to be tested in-situ for a cell density application.

19. The apparatus of claim 18 wherein the processor can control application of the signal to the light source via a change of a level of a current supplied to the light source.

20. The apparatus of claim 18 wherein either or both of the detectors comprise photodiodes.

21. The apparatus of claim 18, further comprising a storage unit coupled to the processor and having software to provide a plurality of reference values.

22. The apparatus of claim 18, further comprising a lookup table stored in the storage unit to store the plurality of reference values, including at least one tolerance value usable to set the predetermined difference.

23. The apparatus of claim 18 wherein the characteristic of the light detected by either or both of the detectors include an intensity of the light.

24. The apparatus of claim 18 wherein the processor can determine whether a malfunction may exist if there is a predetermined difference between obtained absorbance unit value changes associated with the first and second detectors.

25. The apparatus of claim 18 wherein the processor can determine whether a malfunction may exist if there is a difference between a determined absorbance unit value change of either or both the first and second signals and a respective predicted absorbance unit value change.

26. The apparatus of claim 18, further comprising circuitry to allow the processor to control application of the supplied signal and to process signals provided from the detectors.

* * * * *